United States Patent [19]

Eliachar

[11] Patent Number: 4,700,700
[45] Date of Patent: Oct. 20, 1987

[54] ENDOTRACHEAL TUBE

[75] Inventor: Isaac Eliachar, Pepper Pike, Ohio

[73] Assignee: The Cleveland Clinic Foundation, Cleveland, Ohio

[21] Appl. No.: 907,862

[22] Filed: Sep. 15, 1986

[51] Int. Cl.⁴ ............................................ A61M 16/00
[52] U.S. Cl. ................................ 128/207.15; 604/101
[58] Field of Search ................... 128/207.14, 207.15; 604/101

[56] References Cited

U.S. PATENT DOCUMENTS

| 4,091,816 | 5/1978 | Elam | 128/207.15 |
| 4,230,108 | 10/1980 | Young | 128/207.15 |
| 4,327,720 | 5/1982 | Bronson et al. | |
| 4,341,210 | 7/1982 | Elam . | |
| 4,453,545 | 6/1984 | Inoue . | |
| 4,456,011 | 6/1984 | Warnecke . | |
| 4,538,606 | 9/1985 | Whited | 128/207.15 |

OTHER PUBLICATIONS

Xomed Anesthesia Products

Primary Examiner—Henry J. Recla
Attorney, Agent, or Firm—D. Peter Hochberg

[57] ABSTRACT

A cuffed endotracheal tube having an upper, unidirectional inflatable-deflatable cuff located above the larynx on the posterior side of the tube operative when inflated to engage the posterior portion of the pharynx to effect alignment of the tube relative to the opening in the larynx.

13 Claims, 9 Drawing Figures

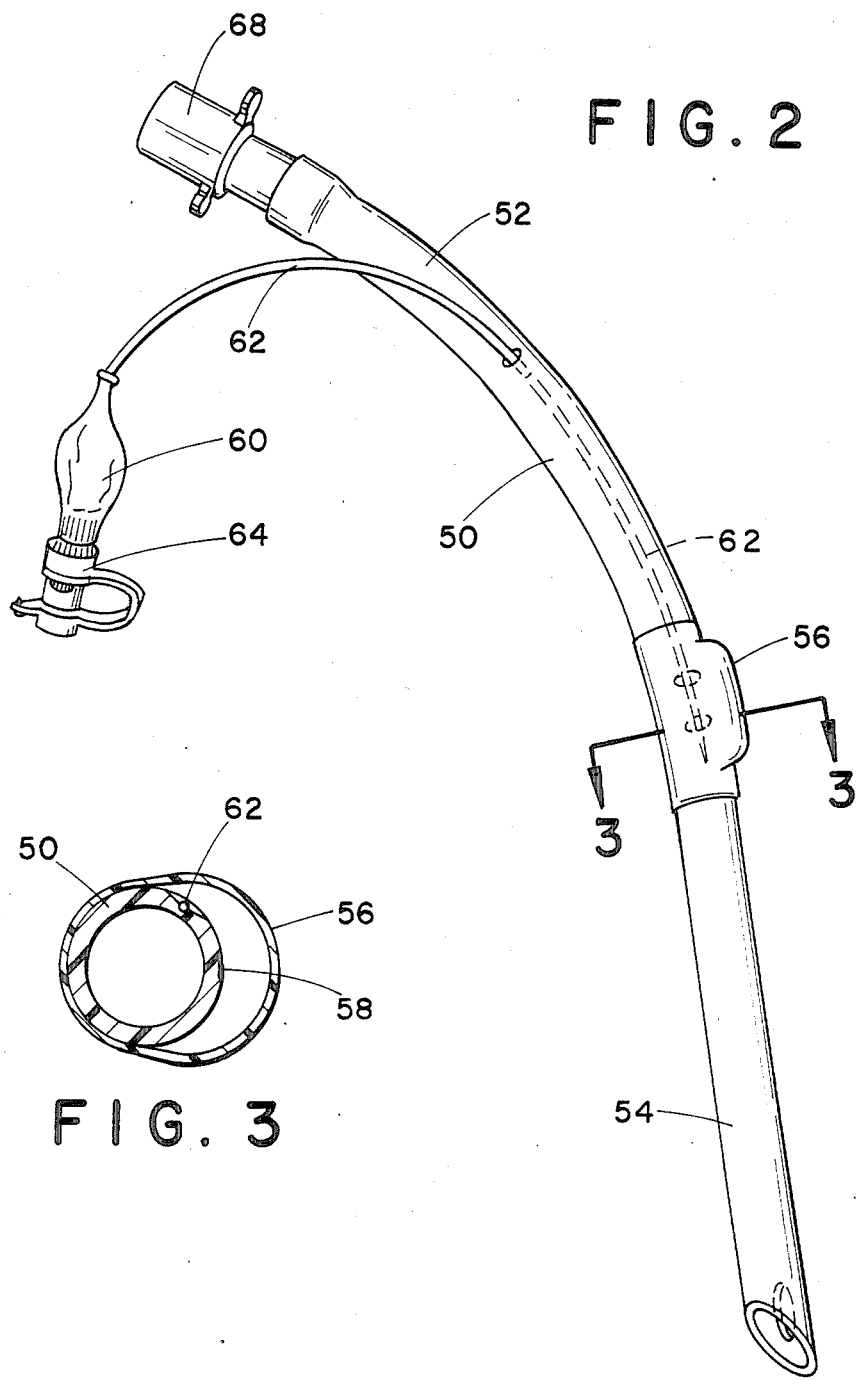

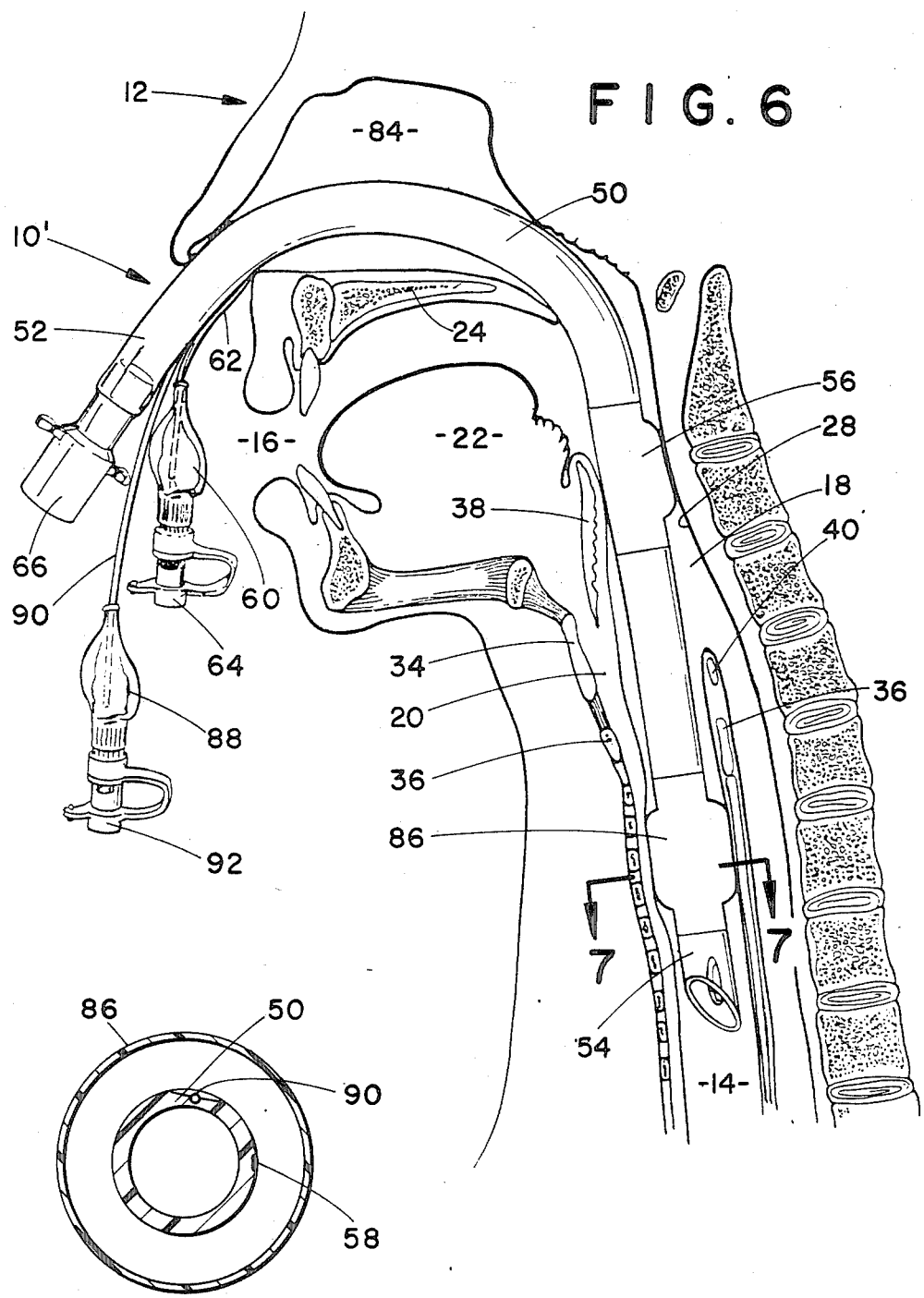

ENDOTRACHEAL TUBE

FIELD OF THE INVENTION

The present invention relates to medical and surgical appliances and more particularly to a tubular device for insertion into the body of a living being, which device includes means for aligning the axis of the tubular device relative to internal body structures. The invention is particularly applicable to an endotracheal tube and will be described with particular reference thereto, although it will be appreciated that the invention has other broader applications.

BACKGROUND OF THE INVENTION

Endotracheal tubes have been known for years and have been routinely employed to prevent upper airway obstruction or to facilitate artificial ventilation of unconscious or anesthetized patients. Such tubes are inserted through the mouth or nasal passage and extend into the trachea of the patient. These tubes generally include an external, resilient sleeve, conventionally referred to as a "cuff", which is inflatable with air following insertion of the device into the human mid-trachea portion. Inflation of the cuff effects an airtight seal of the space between the tube and the surrounding body tissue, i.e., the inner wall of the trachea. The tubular portion of these devices is comprised of a fairly rigid plastic material to prevent the artificial airway from collapsing when in the body.

When inserted into the patient's throat, an endotracheal tube assumes a generally curved, hook shaped configuration to conform to the passage connecting the mouth or nasal cavity with the trachea. In this position, the endotracheal tube necessarily traverses the delicate structures of the larynx, and the stressed, curved configuration of the tube forces it into direct pressure contact with the posterior region thereof. Importantly, this region of the larynx is particularly sensitive in that it is comprised of joints between cartilages and ligaments. Particularly delicate parts of the posterior region of larynx are the arytenoid cartilages which rotate the ventricular ligaments (true vocal cords) and the posterior commissure which comprises the junction of the ventricular ligaments. In this respect, the arytenoid cartilages and posterior commissure may be damaged by prolonged contact and pressure from the endotracheal tube. Still further, engagement of the tube with the posterior mucosa lining of the larynx, associated with the constant movement of the larynx due to swallowing, breathing and mechanically assisted respiration, causes the formation of inflammatory reaction resulting in scar tissue thereon. Such scar tissue once formed is generally permanent, and may obstruct the airway and restrict the movement of the arytenoid cartilages. Attempts to remove it surgically may result in its regrowth.

Either form of damage to the posterior region of the larynx effects speech as well as the ability of the larynx to protect the trachea and lungs from saliva, food and/or other secretions. Accordingly it is extremely important that contact between the endotracheal tube and the posterior region of the larynx be avoided or kept to a minimum during prolonged intubation.

Devices known heretofore, such as those shown in U.S. Pat. Nos. 4,341,210 and 4,091,816 to Elam; 4,327,720 to Bronson et al; and 4,453,545 to Inoue, have generally been concerned with sealing the trachea to prevent secretions in the pharynx from entering the lungs via the larynx and trachea. Some of these devices disclose anchoring the endotracheal tube longitudinally by inflating additional cuffs around the larynx wherein the cuffs are in contact with the larynx itself. In this respect, these prior devices fail to address or consider the axial position of the endotracheal tube relative to the critical posterior region of the larynx, or the injurious effect caused by contact between the larynx and the tube or cuffs on the function of the larynx.

The present invention overcomes these problems by providing an endotracheal airway device wherein the axial position of the tube within the larynx can be modified to reduce or avoid contact between the tube and the delicate posterior region of the larynx, and in particular the aryntenoid cartilages and the posterior commissure.

SUMMARY OF THE INVENTION

In accordance with the present invention, there is provided a tubular device for insertion into the body of a living being, which device includes means for aligning the axis of the tubular device relative to the internal body structure. With respect to one embodiment of the invention there is provided an endotracheal airway device for insertion through a patient's mouth or nasal passage into the trachea to provide a passage for respiration. The device is comprised of an elongated flexible tube having upper and lower end portions wherein the lower end portion is inserted into the mid-trachea portion below the larynx while the upper end portion remains outside the mouth or nasal passage. An upper inflatable-deflatable cuff fixed above the larynx surrounds a predetermined portion of the posterior round of the tube. The upper cuff is operative when inflated to engage the posterior portion of the pharynx to effect an alignment of the tube relative to the larynx wherein the axis of the tube portion within the larynx is maintained central therto such that the tube is away from the posterior portion thereof. The device includes means for inflating and deflating the upper cuffs.

In accordance with another aspect of the present invention, there is provided a device as set forth above including a lower inflatable-deflatable cuff spaced from the upper cuff to be positioned a predetermined distance below the larynx. The lower cuff is opoerative upon inflation to sealingly engage the inner wall of the trachea. Means, separate from the upper cuff, are provided for inflating and deflating the lower cuff.

More specifically, the upper cuff and lower cuff are respectively positioned on a tube such that when inserted into the patient, the upper end of the lower cuff would be a few centimeters below the cricoid arch, and a lower end of the upper cuff would be a few centimeters above the arytenoid cartilages. In this respect, the upper cuff which surrounds only a predetermined portion of the posterior round of the tube is therefore positioned in the pharynx. Means for inflating and deflating the respective cuffs are comprised of separate and distinct channels or ducts within the wall of the tube which extend from the cuffs to the upper end portion of the tube. Appropriate fittings connectable to a syringe are provided for inflation and deflation of the cuffs. The lower cuff has an elongated, cylindrical, barrel-like configuration. This configuration effects axial alignment of the lower portion of the tube with the axis of the trachea. The upper cuff is disposed on the posterior side of the flexible tube to inflate toward the back, posterior surface of the pharynx. In this respect, the upper cuff is generally unidirectional in that it inflates away from the tube in one direction toward the posterior of the pharynx. The upper cuff is operative upon inflation to force the tube toward the epiglottis and tongue to position the tube away from the posterior portion of the larynx. A fully inflated upper cuff preferably extends aproximately 2-3 centimeters from the outer circumferential surface of the tube and displaces the tube from the posterior portion of the pharynx accordingly.

An important aspect of the present invention is that the configuration of the upper cuff allows the physician to monitor the position of the tube in relation to the larynx and modify inflation of the cuff accordingly. In this respect, the upper cuff does not completely occupy and seal the passage through the pharynx, and thus the inflation postion, as well as the condition of the larynx, can be monitored by means of flexible fiber optic scopes inserted around the sides of the upper cuff through the mouth or the nose. In another respect, because the upper cuff does not occupy the full extent of the pharyngeal lumen, it allows passage of other tubes alongside, such as a tube through the esophagus into the stomach. This permits other medical procedures to be conducted during intubation.

It is an object of the present invention to provide an endotracheal airway device which reduces the likelihood of injury to the posterior portion of the larynx during intubation without sifting of injurious potentials to other sites.

It is another object of the present invention to provide an endotracheal airway device which maintains the tubular portion which extends through the larynx away from the delicate members at the posterior of the larynx.

It is another object of the present invention to provide a device as described above wherein such device includes a directional, inflatable cuff on the posterior side of the upper portion of the tube in the pharynx to displace the tube forward toward the tongue.

A still further object of the present invention is to provide a device as described above wherein a lower inflatable-deflatable cuff spaced from the upper cuff is provided below the larynx in the trachea, which lower cuff encircles the tube and is operative upon inflation to sealingly engage the inner wall of the trachea.

A still further object of the present invention is to provide an endotracheal tube as described above wherein the upper, directional cuff does not completely seal the pharyngeal region and thereby provides a pasageway into the larynx wherein fiber optic scopes can be used to monitor the condition of the larynx.

These and other objects and advantages will become apparent from the following description of a preferred embodiment taken together with the accompanying drawings.

DRAWINGS

The invention may take physical form in certain parts and arrangements of parts, preferred embodiments which will be described in detail in the specification and illustrated in the accompanying drawings wherein:

FIG. 2 is a view illustrating the endotracheal tube shown in FIG. 1 removed from the patient;

FIG. 3 is an enlarged cross-sectional view taken along line 3—3 in FIG. 2 showing a sectional view of the upper cuff when fully inflated;

FIG. 6 is a sectional, partially schematic view of the endotracheal tube illustrating a second embodiment of the present invention installed through the nasal passage of the patient, which tube includes a lower cuff below the larynx to sealingly engage the trachea; and FIG. 7 is an enlarged cross-sectional view taken along line 7—7 of FIG. 6 showing the lower cuff when fully inflated.

DETAILED DESCRIPTION OF PREFERRED EMBODIMENT

Figure 1:
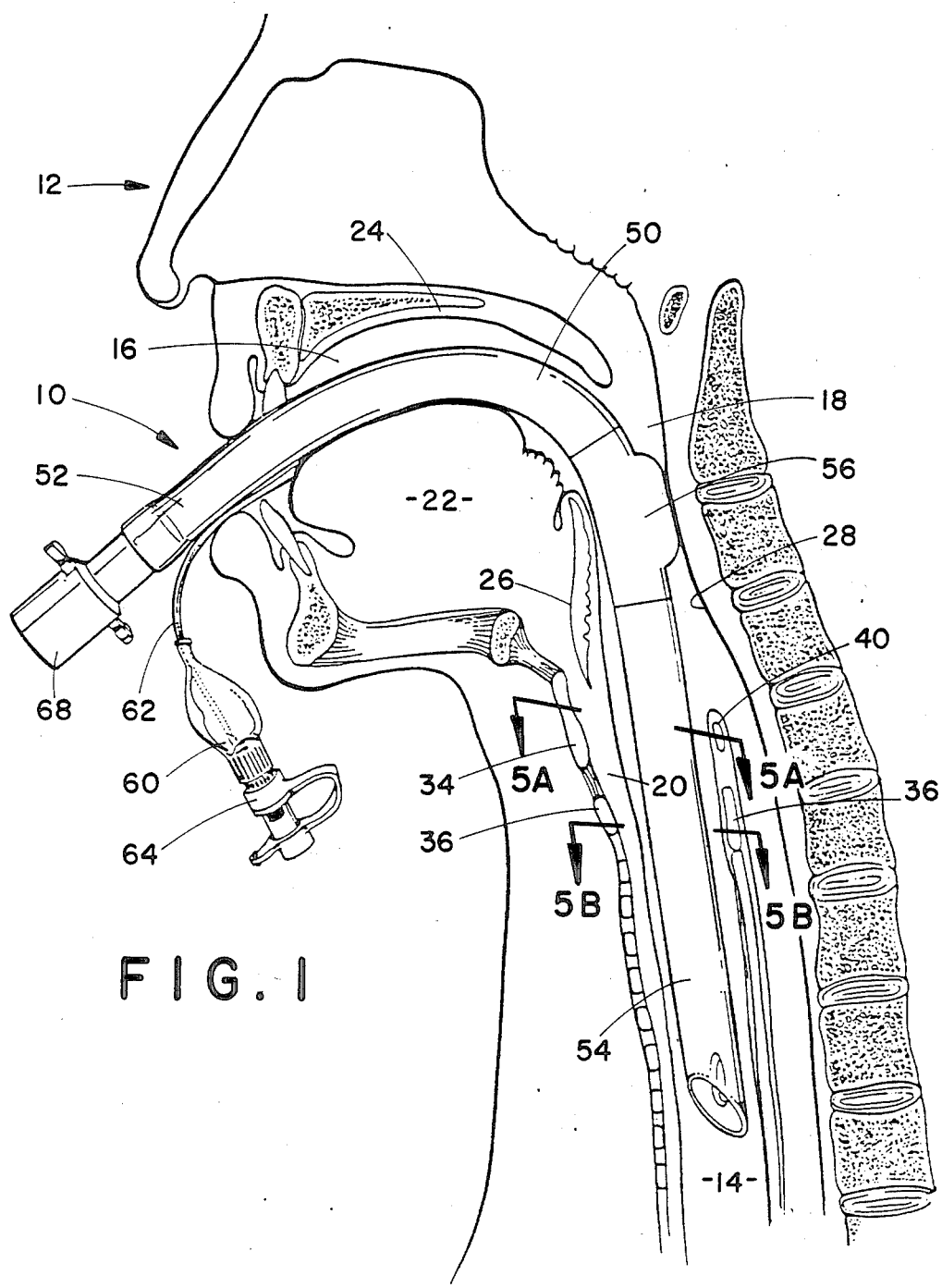
FIG. 1 is a sectional, partially schematic view of an endotracheal tube illustrating a preferred embodiment of the present invention installed through the mouth of a patient, which tube includes an upper cuff located above the larynx inflated to maintain the tube from contact with the posterior region of the larynx.

Referring now to the drawings wherein the showing is for the purpose of illustrating preferred embodiments of the invention only and not for the purpose of limiting same, FIG. 1 shows a cuffed endotracheal device 10 in accordance with an embodiment of the present invention positioned within a patient designated 12. Tube 10 is shown inserted into the trachea 14 through the mouth 16 and pharynx 18. In this position, the tube extends through the larynx designated 20 and is disposed between the tongue 22 and palate 24, and between epiglottis 26 and the posterior wall 28 of pharynx 18. As shown in the drawings, endotracheal device 10 assumes a generally curved, hook-shaped configuration corresponding to the passage through mouth 16, pharynx 18 and trachea 14.

Figures 4A, 4B:
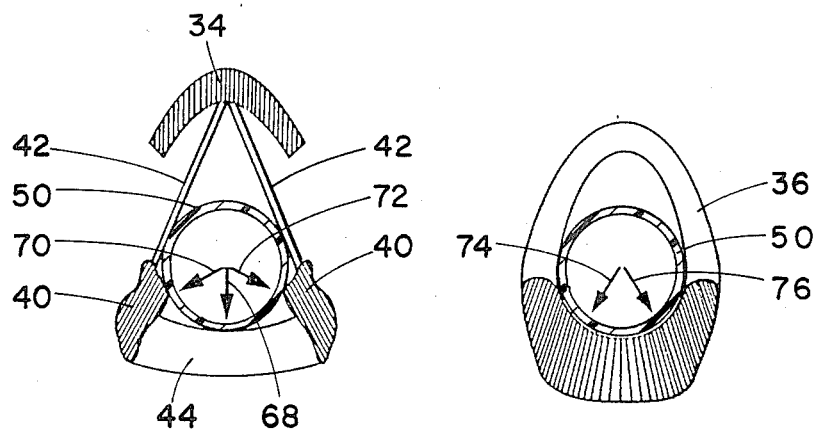
FIGS. 4A and 4B are cross-sectional views looking downward through the thyroid and the cricoid level of the larynx respectively illustrating the typical position of an uncuffed endotracheal tube pressing against the posterior portion of the larynx.

Referring now to FIGS. 1, 4A, 4B, and 5B larynx 20 will be described to provide a clearer understanding of the present invention. In general, the larynx 20 includes three single cartilages, the thyroid 34, the cricoid 36 and the epiglottis 26 together with three paired cartilages, the arytenoid 40, the corniculate (not shown) and the coneiform (not shown). The thyroid cartilage 34, which is the largest of these cartilages, forms the anterior part of the larynx and is shaped somewhat like the cover of an open book with the back of the hook forming the prominent projection in the neck (Adam's apple). The cricoid cartilage 36 is shaped like a signet ring, with the signet part posterior and the arch anterior. The epiglottis 26 is a leaf-like cartilage. The arytenoid cartilages 40 are two small pyramid-shaped masses crowning the signet part of the cricoid 36 at the back or posterior of larynx 20. The corniculate cartilages (not shown) are two very tiny cones, one placed on the apex of each arytenoid cartilage 40. The cuneiform cartilages (not shown) are two extremely tiny rods in the mucous membrane fold joining the epiglottis 26 to the arytenoids cartilages 40. The vocal ligaments or cords 42, illustrated in FIGS. 4A or 5A, are comprised of soft tissue covered by a mucosa lining, and extend from the thyroid 34 to each arytenoid cartilage 40. The arytenoid cartilages 40 articulate with the cricoid 36 to rotate the vocal cords 42 to produce sound. The cricoid 36 is an important structure in the larynx in that it serves as a platform or base for the entire larynx 20. The posterior commissure 44, illustrated in FIGS. 4A or 5A, extends between the arytenoid cartilages 40 on the posterior side of larynx 20.

Referring now to FIG. 2, endotracheal device 10 includes an elongated flexible tube 50 having an upper end portion 52 adapted to be located external mouth 16 and a lower end portion 54 adapted to be located within trachea 14. An inflatable-deflatable upper cuff 56 is provided on tube 50 intermediate upper and lower end portions 52, 54. Upper cuff 56 is asymmetrical with respect to tube 50, in that it surrounds a circumferential portion of the posterior side thereof and extends when inflated toward the posterior wall 28 of the pharynx 18. Cuff 56 is dimensioned to extend a predetermined distance from tube 50 wherein cuff 56 is operative to shift tube 50 away from the posterior wall 28 of the pharynx 18 forward toward tongue 22 and epiglottis 26. In this respect, upper cuff 56 acts as a spacer to shift tube 50 away from the posterior portion of the larynx 20, specifically the arytenoid cartilages 40 and the posterior commissure 44. Further with respect to the dimensions of cuff 56, the surface portion of cuff 56 engaging the posterior wall 28 of the pharynx 18 should be of sufficient width and length so as to ensure no damage to the pharynx from localized, excessive pressure.

Inflation means 60 are provided for inflating and deflating cuffs 56. Inflation means 60 is comprised of a duct or channel 62 within the wall of tube 50. Duct 62 leads from cuff 56 to upper end portion 52 and a syringe connector 64. Connectors of this type are conventionally known in the medical field. In this respect, connector 64 in and of itself forms no part of the present invention and therefore will not be described in detail. The upper end portions 52 preferably includes a standard, universally known adaptor 66 attachable to a respirator or the like.

To ensure proper positioning of the tube locating means 58, best seen in FIGS. 3 and 7, are provided on tube 50. The locating means may be comprised of any marking or indicator arrows but is preferably a radio opaque line extending the entire length of the tube symmetrical to cuff 56. With locating means 58, alignment of cuff can be visualized clinically or by x-ray techniques.

With respect to the embodiment shown, tube 50 is preferably comprised of a biocompatible silicon material which can be autoclaved, and cuff 56 is preferably comprised of a low pressure soft silicon material to effect minimal or no trauma or tracheal or pharyngeal tissue. Preferably cuff 56 is attached integrally to tube 50.

Referring now to the operation of device 10, as set forth above, when inserted into a patient 12, an endotracheal tube assumes a generally curved, hook-shaped configuration conforming to the passage defined by the mouth 16, the pharynx 18 and trachea 14. In this configuration, the ragidity of the tube portion would press conventionally known endotracheal tubes against the posterior of larynx 20, specifically the posterior commissure 44 and the arytenoid cartilages 40. This condition is illustrated in FIG. 4A, wherein the points of maximum stress against the arytenoid cartilages 40 are indicated by arrows 70, 72 and the point of maximum stress against the posterior commissure 44 is indicated by arrows 68. FIG. 4B illustrates the position of the tube against the mucosa lining of the posterior portion of the cricoid cartilage 36, and the points of maximum stress are indicated by arrows 74, 76. These direct pressure contacts may damage the delicate cartilage structure or generate pressure sores which may compromise the voice and the airway. With the present invention however the position of the axis of the tube can be aligned by inflation of cuff 56. In this respect, the device 10 with cuff 56 deflated, is inserted through the mouth 16 such that lower end portion 54 is located in the trachea 14. Upper cuff 56 is preferably positioned at least 2 centimeters above larynx 20. Upper cuff 56 is provided to overcome the curvature of the tube, as well as the effect tongue 22 and epiglottis 26 have on tube 50, which force it against the posterior region of larynx 20. Cuff 36 is inflated by injecting air into inflation means 60 by a syringe. Importantly, cuff 56 can be partially or totally inflated to selectively position the upper portion of tube 50 relative to larynx 20. In this respect, the asymmetrical position of cuff 56 relative to tube 50 acts as a pillow when inflated to shift the axis of tube 50 in the area of larynx 20 away from the posterior region thereof, specifically the arytenoid cartilages 40, the posterior commissure 44, and the mucosa lining of the cricoid cartilage 36.

Figures 5A, 5B:
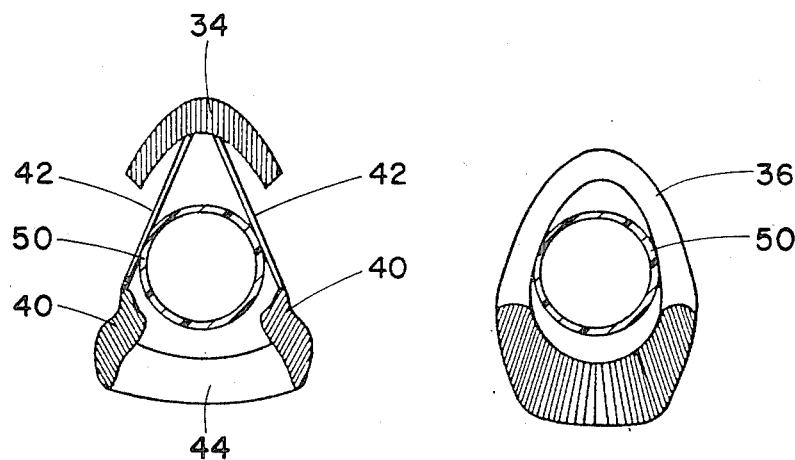
FIGS. 5A and 5B are cross-sectional views taken along lines 5A—5A and 5B—5B of FIG. 1 showing an endotracheal tube according to the present invention maintained away from the posterior portion of the larynx.

The advantages of the present invention can be best seen in FIGS. 5A and 5B, which illustrate how tube 50 is positioned away from the posterior of the larynx 20. By moving tube 50 to a central position within the larynx 20, the likelihood of damage to the critical arytenoid cartilages 40, the posterior commissure 44 and the cricoid cartilage 36 is substantially reduced.

Because upper cuff 56 does not occupy the entire lumen of the larynx 20, flexible fiber optic scopes may be inserted along side cuff 56 or tube 50 which enables the physician to monitor the position of tube 50 relative to larynx 20 during inflation of cuff 56. This allows the physician to adjust the position of tube 50 to effect minimal contact between tube 50 and larynx 20. This procedure can also be used to examine the relative position of cuff 56 above larynx 20 to assure proper positioning thereof and to ensure no contact between cuff 56 and larynx 20 during intubation. In addition to fiber optic scopes, tubes may also be inserted along side cuff 56. For example, a tube may be inserted into the stomach through the esophagus 80, or a suction tube may be inserted into the pharynx 18 to collect secretions and to prevent same from entering the lungs through the larynx 20 via trachea 14.

Accordingly there is provided an endotracheal tube which is positionable in the patient by means of a unidirectional cuff 56 to prevent injury to the patient's larynx from prolonged intubation. It will be appreciated that the dimensions of device 10, i.e., the diameter of tube 50 and the size of cuff 56 will depend on the size of the patient. In this respect, the dimensions will be smaller for a child as compared to an adult.

In one respect, the upper cuff may have segmented into separate compartments (not shown), each compartment having a distinct and separate inflation means. In other words, the cuff 56 shown in the drawings could have two separate, side-by-side chambers, each of which is separately inflatable. In addition to the forward correction effected by inflation of such a cuff, the compartments of a segmented cuff could be inflated separately to induce a slight side-to-side correction of the axis of the tube relative to the larynx 20.

Referring now to FIG. 6, a second embodiment of the present invention, designated 10', is shown positioned in patient 12 through the nasal passage 84. Endotracheal device 10' is preferably similar to the embodiment described heretofore with the exception that a lower inflatable-deflatable cuff 86 which encircles tube 50 is provided adjacent to the lower end portion 54. Lower cuff 86 is elongated, generally cylindrical or barrel-like in shape, and dimensioned to fully occupy the tracheal lumen when inflated. In this respect, its shape when inflated approximates the intertracheal passage with only slight contact so as not to damage the body tissue. The contact however is sufficient to seal the tracheal tube and to centrally position tube 50 relative to the axis of the trachea 14. FIG. 7 shows a enlarged sectional view of lower cuff 86 when fully inflated. Lower cuff 86 is spaced from upper cuff 56 to position it a few (preferably 7-8) centimeters below the larynx 20 when device 10' is inserted in patient 12. Inflation means 88, comprised of duct or channel 90 and standard syringe connector 92, are provided for inflating and deflating lower cuff 86. Inflation means 88 are preferably similar to those described above for upper cuff 56, but are separate and distinct therefrom to allow separate inflation of the respective cuffs.

In operation, device 10 with cuffs 56, 86 deflated is inserted through the nasal passage 84 such that lower end portion 52 of tube 50 is located in the trachea 14. Lower cuff 86 is positioned a few, approximately 7-8, centimeters below the larynx 20. Lower cuff 56 is then inflated by injecting air through inflation means 88, i.e., duct 90 and connector 92. The configuration of lower cuff 86 when inflated approximates, with slight sealing contact, the tubular shape of the trachea 14. The elongated, barrel-shape configuration contributes to alignment of tube 50 with respect to larynx 20. In this respect, lower cuff 86 generally align the axis of the lower end of tube 50 with the axis of trachea 14. In conjunction with the operation of upper cuff 56, lower cuff 86 provides more stable positioning of tube 50 in larynx 20. With both cuff 56, 86 inflated the likelihood of movement by tube 50 in larynx 20 is reduced.

Device 10' is shown in FIG. 6 as being inserted through the nasal passage 84. Insertion of the device in this manner reduces the bend and stress in tube 50, as seen in FIGS. 1 and 6. It will of course be apreciated that either embodiment of the present invention may be inserted either through mouth 16 or nasal passage 84.

The present invention has been described with respect to preferred embodiments. Modifications and alterations will occur to others upon the reading and understanding of this specification. It is intended that all such modifications and alterations be included insofar as they come within the scope of the patent as claimed or the equivalents thereof.

Having thus described the invention, the following is claimed:

1. A cuffed endotracheal tube for insertion through the mouth and into the trachea of a patient to provide a passage for artificial respiration comprising:
   an elongated flexible tube having an upper end portion adapted to be located external to the mouth and a lower end portion adapted to be located in the trachea;
   a lower inflatable-deflatable cuff located along said tube relative to said lower end portion thereof, said lower cuff encircling said tube a predetermined distance below the larynx and operative upon inflation to sealingly engage the inner wall of said trachea below said larynx;
   an upper inflatable-deflatable cuff located along said tube a predetermined distance from said lower cuff to locate said upper cuff above said larynx, said upper cuff mounted partially on the said tube on a predetermined portion of the posterior round thereof, thereby defining a cuffed side of said tube facing the posterior portion of the pharynx and an uncuffed side of said tube facing the epiglottis, said upper cuff operative when inflated to extend outwardly from said tube to engage the posterior portion of the pharynx to move said uncuffed side of said tube toward the epiglottis said movement effecting alignment of said tube relative to the laryngeal passage to prevent contact between said tube and the posterior region of said larynx; and
   means for separately inflating and deflating the upper and lower cuffs, said cuffs dimensioned to avoid contact with the larynx when inflated and positioned in the patient.

2. A tube as defined in claim 1 wherein said means of inflating comprises separate channels within the wall of said tube extending from said cuffs to the upper end portion of said tube.

3. A tube as defined in claim 1 wherein said upper and lower cuffs are spaced from each other a distance sufficient to maintain said cuff away from said larynx.

4. A tube as defined in claim 1 wherein the lower end of said upper cuff is at least 2 centimeters above the arytenoid cartilage and the upper end of said lower cuff is 5 to 6 centimeters below the cervical trachea when said tube is within said patient.

5. An endotracheal airway device for insertion through a patient's mouth into the trachea to provide a passage for respiration, said device comprising:
   an elongated flexible tube having first and second distal ends, said first end for insertion into a mid trachea position below the larynx with said second end remaining outside the mouth;
   a lower inflatable cuff encircling said tube fixed a predetermined distance below said larynx, said lower cuff operative upon inflation to sealingly engage the inner wall of said trachea;
   an upper inflatable cuff fixed above said larynx in the pharynx mounted to a predetermined portion of the posterior round of the tube thereby defining a cuffed side of said tube facing the posterior portion of the pharynx and an uncuffed side of said tube facing the epiglottis, said upper cuff operative when inflated to engage the posterior portion of the pharynx and move said uncuffed side of said tube toward the epiglottis, said movement effecting an alignment of the tube between said cuffs with the axis of the trachea wherein said tube portions within said larynx is maintaining central thereto and away from the posterior portion thereof; and,
   means for inflating and deflating said cuffs.

6. An endotracheal airway device for insertion through a patient's mouth or nasal passage into the trachea to provide a passage for respiration, said device comprising:
   an elongted flexible tube having first and second distal ends, said first end for insertion into a mid tracheal position below the larynx with said second end remaining outside the mouth or nasal passage;
   a first inflatable-deflatable cuff intermediate said first and second distal ends, mounted partially around said tube to define a cuffed side and an uncuffed side of said tube, said first cuff positionable above the larynx with said cuffed side facing the posterior surface of the pharynx and dimensioned to operatively engage said posterior surface when inflated to effect a shift of said tube away therefrom wherein said tube portion within the larynx may be positioned away from the posterior portion thereof; and means for inflating and deflating said first cuff.

7. A device as defined in claim 6 wherein said cuff when fully inflated extends approximately 2-3 centimeters from the surface of said tube.

8. A device as defined in claim 6 wherein said tube and said cuff are of a silicone composition.

9. A device as defined in claim 6 wherein said means for inflating comprises a duct within the wall of said tube extending from said cuff to said second end of said tube.

10. A device defined in claim 6 further comprising: a second inflatable-deflating cuff spaced from said first cuff positionable below said larynx, and second cuff encircling said tube and operative when inflated to sealingly engage the inner wall of the trachea; and means for inflating and deflating said second cuff.

11. A device as defined in claim 10 wherein said means for inflating said second cuff are separate from said means for inflating said first cuff.

12. A device as defined in claim 10 wherein said second cuff is integrally formed on said tube.

13. A device as defined in claim 6 wherein said first is integrally formed on said tube.

* * * * *